(12) United States Patent
Choi et al.

(10) Patent No.: US 10,197,790 B2
(45) Date of Patent: Feb. 5, 2019

(54) METHOD OF ENHANCING TRANSMISSION CHARACTERISTICS OF WAVES AND DEVICE OF PERFORMING PREDETERMINED FUNCTION BY INTRODUCING WAVES ONTO DISORDERED MEDIUM

(71) Applicant: KOREA UNIVERSITY RESEARCH AND BUSINESS FOUNDATION, Seoul (KR)

(72) Inventors: Won-Shik Choi, Seoul (KR); Won-Jun Choi, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 278 days.

(21) Appl. No.: 15/103,941

(22) PCT Filed: Feb. 26, 2014

(86) PCT No.: PCT/KR2014/001562
§ 371 (c)(1),
(2) Date: Jun. 13, 2016

(87) PCT Pub. No.: WO2015/088103
PCT Pub. Date: Jun. 18, 2015

(65) Prior Publication Data
US 2016/0349500 A1 Dec. 1, 2016

(30) Foreign Application Priority Data
Dec. 13, 2013 (KR) ........................ 10-2013-0155312

(51) Int. Cl.
*A61B 18/20* (2006.01)
*G02B 26/06* (2006.01)
*A61B 18/00* (2006.01)

(52) U.S. Cl.
CPC .............. *G02B 26/06* (2013.01); *A61B 18/20* (2013.01); *A61B 18/203* (2013.01);
(Continued)

(58) Field of Classification Search
CPC ............ A61B 18/20; A61B 2018/2035; A61B 18/203; A61B 2018/00452;
(Continued)

(56) References Cited

U.S. PATENT DOCUMENTS 3,904,274 A * 9/1975 Feinleib ................. G02B 26/06
310/328
4,146,307 A * 3/1979 Gaffard ................. G01S 7/4816
359/224.1
(Continued)

FOREIGN PATENT DOCUMENTS

JP       6-181358 A       6/1994
JP    2003-332658 A    11/2003
(Continued)

OTHER PUBLICATIONS

Tuchin, Valerii Viktorovich. "Light scattering study of tissues." Physics-Uspekhi 40.5 (1997): 495-515. (22 pages in English).
(Continued)

*Primary Examiner* — Bumsuk Won
*Assistant Examiner* — Balram T Parbadia
(74) *Attorney, Agent, or Firm* — NSIP Law

(57) ABSTRACT

A method of enhancing transmittance of waves according to the invention comprises the following steps: (a) generating a plurality of waves each of which has random phase; (b) grouping randomly the plurality of waves into a first group and a second group; (c) introducing the waves onto a disordered medium by fixing phase of waves constituting the first group and varying phase of waves constituting the second group; (d) measuring intensity of the waves based on
(Continued)

overlapped waves of the first group and the second group which penetrated the disordered medium according to the phase variation of waves constituting the second group; (e) obtaining phase having the maximum intensity according to the phase variation among intensities measured at the step (d); and (f) adjusting phase of the waves constituting the second group based on phase obtained at the step (e).

10 Claims, 7 Drawing Sheets

(52) U.S. Cl.
CPC .............. *A61B 2018/00452* (2013.01); *A61B 2018/00785* (2013.01); *A61B 2018/00869* (2013.01); *A61B 2018/204* (2013.01); *A61B 2018/2035* (2013.01)

(58) Field of Classification Search
CPC .......... A61B 2018/00785; A61B 2018/00869; A61B 2018/204; A61B 5/0066; A61B 3/102; G02B 26/06; G01B 9/02; G01B 11/2441; G01N 21/4795
See application file for complete search history.

(56) References Cited

U.S. PATENT DOCUMENTS

| 2009/0161090 A1* | 6/2009 | Campbell ............ A61B 3/0091 356/3 |
| 2009/0208072 A1* | 8/2009 | Seibel ................ G01N 21/4795 382/128 |
| 2011/0149239 A1* | 6/2011 | Neal .................... A61B 3/0025 351/205 |

FOREIGN PATENT DOCUMENTS

KR         10-0658493 B1    12/2006
KR    10-2009-0061777 A     6/2009

OTHER PUBLICATIONS

Choi, Wonjun, et al. "Transmission eigenchannels in a disordered medium." Physical Review B 83.13 (2011): 134207-1 ~ 134207-5 (7 pages in English).
International Search Report dated Sep. 12, 2014 in counterpart International Application No. PCT/KR2014/001562 (7 pages in Korean with English translation).

* cited by examiner

FIG. 5
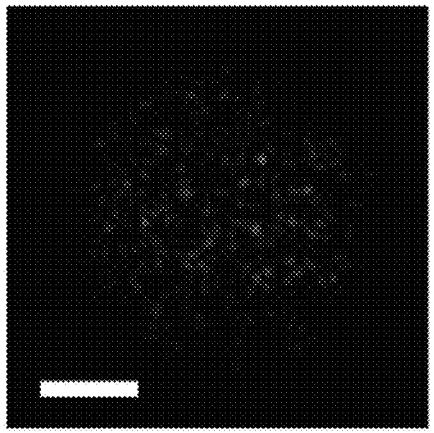
(a)
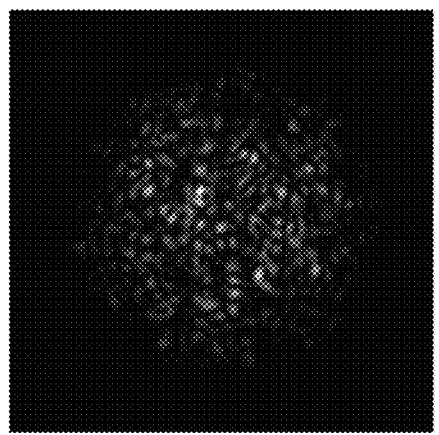
(b)

METHOD OF ENHANCING TRANSMISSION CHARACTERISTICS OF WAVES AND DEVICE OF PERFORMING PREDETERMINED FUNCTION BY INTRODUCING WAVES ONTO DISORDERED MEDIUM

CROSS REFERENCE TO RELATED APPLICATION(S)

This application is a National Phase entry of PCT Application No. PCT/KR2014/001562, filed on Feb. 26, 2014, which claims priority under 35 U.S. C. § 119(e), 120 and 365(c) to Korean Patent Application No. 10-2013-0155312, filed on Dec. 13, 2013, in the Korean Intellectual Property Office, the entire disclosures of each of which are incorporated herein by reference for all purposes.

TECHNICAL FIELD

The invention relates to a method of enhancing transmission characteristics of waves and device of performing predetermined function by introducing waves onto a disordered medium and in particular a method of enhancing transmission characteristics of waves and device of performing predetermined function by introducing waves onto a disordered medium for transferring more waves into the disordered medium or the opposite.

BACKGROUND ART

Devices of performing certain function by introducing wave onto a disordered medium are being widely used. For example, in case of skin therapy using light of laser, the devices are widely used for removing abnormal cells in the human skin which is a disordered medium and also used for inspecting the inside of metal or buildings by means of waves.

Generally, when wave is incident on the disordered medium, multiple scattering is generated in the medium and thus intensity of wave decreases as the penetration depth of incident wave in the medium increases.

The decrease of intensity of wave according to the increase of penetration depth of wave causes bad effects on the actual application using wave. For example, for the removal of abnormal cells in the skin, laser with a certain intensity having must penetrate into the depth where abnormal cells exist. Considering the decrease of intensity, if intensity of laser is increased, skin not to be removed which extends to the abnormal cell may be damaged. Therefore, techniques for enhancing transmission characteristics of wave are required.

Regarding the enhancement of transmission characteristics of wave, it is proved that when wavefront of incident wave is adjusted, the reduction of reflection on the disordered medium allows the increase of the penetrating depth of wave in the disordered medium.

According to the above theory, wavefront of incident wave for the above effect varies according to the disordered medium and it is an issue to find such wavefront. As of now, regarding a method of finding wavefront of incident wave, a single point optimization method and a method using scattering matrix measurement are known.

According to the single point optimization method, wavefront of incident waves is controlled such that incident waves physically orthogonal to each other are simultaneously introduced into the disordered medium and then, waves which emitted from the penetrating surface of the disordered medium has constructive interference at one point. Since the single point optimization method increases the total intensity of penetrating waves by increasing intensity of wave at one point, it is disadvantageous that the increase of intensity of penetrating wave is not substantial. Further, in the single point optimization method, disadvantageously, intensity of wave at the penetrating surface must be measured to increase the penetrating depth of wave, i.e., to increase intensity of penetrating wave.

Meanwhile, in the method using scattering matrix measurement, when waves physically orthogonal to each other are introduced into the disordered medium, amplitude and phase of scattering wave by the disordered medium are measured and is made in the form of a matrix, and then wavefront of wave whose transmittance is increased is found by analyzing the matrix.

The method of scattering matrix measurement is divided into a method of using a transmission matrix and a method of using a reflection matrix. In case of the method of using a transmission matrix, amplitude and phase of waves emitting from penetrating surface of the disordered medium are measured two-dimensionally to obtain a transmission matrix, like the single point optimization method. Meanwhile, in case of a method of using a reflection matrix, amplitude and phase of waves reflected by the disordered medium are measured two-dimensionally to obtain a transmission matrix and then, the transmittance is increased by finding wavefront of incident wave having the minimum reflection.

It is advantageous that the method of scattering matrix measurement has higher increase of penetrating wave that the single point optimization method and can also use selectively transmission wave and reflective wave.

The method of scattering matrix measurement is divided into a method of using a transmission matrix and a method of using a reflection matrix. However, to obtain a matrix, information of amplitude and phase of wave must be obtained at the penetrating surface of scattering wave and the measurement of both amplitude and phase of wave at many points inside the surface is very difficult and it costs a lot.

Also, besides the disadvantages or problems of the measurement, the above two methods have problems of difficulty to apply the methods to the actual devices such as a laser treatment equipment. Skin has different transmission characteristics depending on people and even for the same people, depending on portions of skin. Therefore, every time treatment is made on a certain portion of skin of a certain person, an adequate wavefront of wave for the corresponding skin must be measured. For the single point optimization method and the method of scattering matrix measurement using transmission matrix, sensor must be embedded in the skin for the measurement and thus, it is actually difficult to apply the method.

Even in a method of scattering matrix measurement using reflection matrix, as described above, since both amplitude and phase of two-dimensional wave at the reflection surface in the disordered medium must be measured, the measurement is difficult and actually, it is difficult to apply the method to laser treatment equipment requiring a real-time measurement.

DISCLOSURE OF THE INVENTION

Technical Problem

The invention is intended to solve the above problems and provides a method of enhancing transmission characteristics of wave by measuring only intensity of wave at the surface where wave penetrates and increasing a penetrating depth according to the reduction of reflection, and a device of performing predetermined function by introducing wave onto a disordered medium.

Also, another object of the invention is to provide a method of enhancing transmission characteristics of wave to increase a penetrating depth of wave by selectively measuring any one of the reflection or transmission without using scattering matrix and a device of performing predetermined function by introducing wave onto a disordered medium.

Technical Solution

The object of the invention may be accomplished by a method of enhancing transmittance of waves comprising the following steps: (a) generating a plurality of waves each of which has random phase; (b) grouping randomly the plurality of waves into a first group and a second group; (c) introducing the waves onto a disordered medium by fixing phase of waves constituting the first group and varying phase of waves constituting the second group; (d) measuring intensity of the waves based on overlapped waves of the first group and the second group which penetrated the disordered medium according to the phase variation of waves constituting the second group; (e) obtaining phase having the maximum intensity according to the phase variation among intensities measured at the step (d); and (f) adjusting phase of the waves constituting the second group based on phase obtained at the step (e).

Further, the object of the invention may be accomplished by a method of enhancing transmittance of waves comprising the following steps: (a) generating a plurality of waves each of which has random phase; (b) grouping randomly the plurality of waves into a first group and a second group; (c) introducing the waves onto a disordered medium by fixing phase of waves constituting the first group and varying phase of waves constituting the second group; (d) measuring intensity of the waves based on overlapped waves of the first group and the second group which are reflected by the disordered medium according to the phase variation of waves constituting the second group; (e) obtaining phase having the minimum intensity according to the phase variation among intensities measured at the step (d); and (f) adjusting phase of the waves constituting the second group based on phase obtained at the step (e).

Here, the invention further comprises the following steps: (g) regrouping randomly waves constituting the first group and waves constituting the second group whose phase was adjusted at the step (f) into the first group and the second group; and (h) adjusting phase of waves constituting the regrouped second group by performing the steps (c) to (f) with regard to the regrouped first group and second group, wherein the steps (g) and (h) may be performed at least one time.

Also, the waves comprise light wave; and the steps (a) to (c) may be performed by a spatial light modulator (SLM) or a digital micro-mirror device.

Further, the waves may comprise at least one of electromagnetic wave, material wave and sound wave.

Also, during the step (f), phase of waves constituting the second group may be adjusted by an amount of phase obtained at the step (e).

Meanwhile, according to the another embodiment, the object of the invention may be accomplished by a device of performing predetermined function by introducing waves onto a disordered medium, comprising: a wave generating unit which generates a plurality of waves having random phase; a wave measuring unit which measures intensity of waves reflected by the disordered medium; and a controller which controls the wave generating unit based on intensity of waves measured by the wave measuring unit; and wherein the controller is configured to: (A) group randomly the plurality of waves generated by the wave generating unit into a first group and a second group; (B) control the wave generating unit such that phase of waves constituting the first group is fixed and phase of waves constituting the second group is varied; (C) control the wave measuring unit such that the wave measuring unit measures intensity of the waves based on overlapped waves of the first group and the second group according to phase variation of waves constituting the second group; and (D) control the wave generating unit such that phase having the minimum intensity according to the phase variation among intensities measured by the wave measuring unit is obtained and phase of the waves constituting the second group is adjusted based on the obtained phase.

Here, the controller may be configured to: (E) regroup randomly waves constituting the first group and waves constituting the second group whose phase was adjusted into the first group and the second group; and (F) control the wave generating unit such that phase of waves constituting the regrouped second group is adjusted by performing the steps (B) to (D) with regard to the regrouped first group and second group; and wherein the steps (E) and (F) may be performed at least one time.

Also, the device may be configured to perform predetermined function; and wherein the wave generating unit comprises a light source illuminating light; and a phase modulator which reflects light from the light source and generates a plurality of waves and which is able to adjust phase of each light wave.

Here, the phase modulator may comprise a spatial light modulator (SLM) or a digital micro-mirror device.

Also, the device may be configured to perform predetermined function by at least one of electromagnetic wave, material wave and sound wave.

Further, the controller may control the wave generating unit such that phase of waves constituting the second group is adjusted by an amount of phase obtained at the step (D).

Advantageous Effect

According to the above features, a method of enhancing transmission characteristics of wave to increase a penetrating depth according to the reduction of reflection by measuring only intensity of wave at the surface where wave is reflected and a device of performing predetermined function by introducing wave onto a disordered medium are provided.

In one example, when a method of enhancing transmission characteristics of wave according to the invention is used for skin care, the skin damage is minimized and the treatment of target under skin can be available by measuring intensity of light reflected by skin to improve the transmission characteristics of skin and adjusting phase in real-time with patterns of enhancing transmission characteristics.

Also, transmission characteristics of wave can be enhanced by increasing a penetrating depth of wave by selectively measuring any one of the reflection or transmission without using scattering matrix.

BRIEF DESCRIPTION OF THE DRAWINGS

FIG. 5 represents an effect of a method of enhancing transmission characteristics of wave according to the invention.

BEST MODE FOR CARRYING OUT THE INVENTION

The method of enhancing transmittance of waves according to the invention comprises the following steps: (a) generating a plurality of waves each of which has random phase; (b) grouping randomly the plurality of waves into a first group and a second group; (c) introducing the waves onto a disordered medium by fixing phase of waves constituting the first group and varying phase of waves constituting the second group; (d) measuring intensity of the waves based on overlapped waves of the first group and the second group which penetrated the disordered medium according to the phase variation of waves constituting the second group; (e) obtaining phase having the maximum intensity according to the phase variation among intensities measured at the step (d); and (f) adjusting phase of the waves constituting the second group based on phase obtained at the step (e).

MODE FOR CARRYING OUT THE INVENTION

Hereinafter, embodiments according to the invention will be explained in detail referring to the attached drawings.

Figure 1:
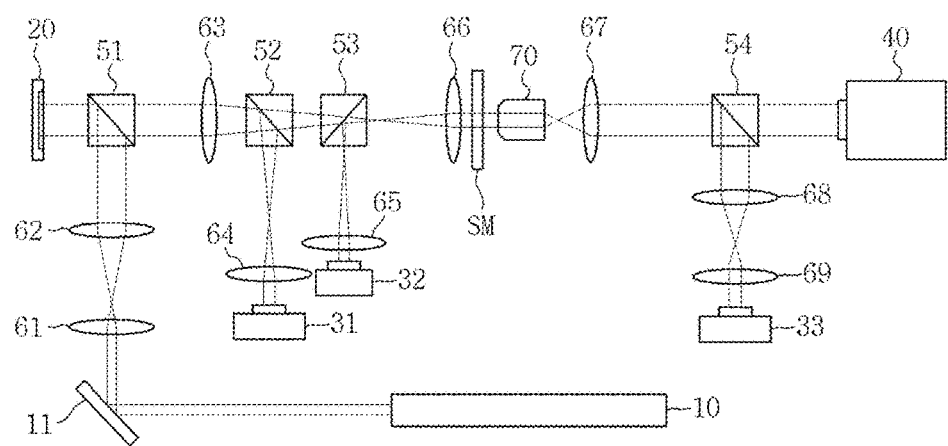
FIG. 1 shows an example of a device to measure an intensity of wave which penetrated and/or is reflected by a method of enhancing transmission characteristics of wave according to the invention.

FIG. 1 shows a device to measure an intensity of wave which penetrates and/or which is reflected by a method of enhancing transmission characteristics of wave according to the invention. For example, in FIG. 1, light wave, i.e., light, is used as wave and hereinafter, a method of enhancing transmission characteristics of wave according to the invention will be explained with light.

Referring to FIG. 1, light irradiated from a light source 10 is reflected by a reflective mirror 11 to change light path and then propagates toward a first beam splitter 51. At least one lens 61, 62 is arranged between the first beam splitter 51 and the reflective mirror 11 such that light from the light source 10 becomes parallel light. In the embodiment, a He—Ne laser light source 10, 111 is used as a light source 10, but the light source is not limited to this.

Light irradiated from the light source 10 and introduced into the beam splitter propagates toward a spatial light modulator 20 (SLM) and then is reflected by the spatial light modulator 20, in particular reflected such that light is divided into a plurality of waves.

The spatial light modulator 20 consists of a number of pixels consisting of liquid crystals. The rotation of the liquid crystal constituting each pixel delays phase of light. Here, in the measuring device according to the invention, when each pixel constituting the spatial light modulator 20 reflects light, phase is adjusted such that phase of waves reflected by the spatial light modulator 20 is adjusted respectively.

In the embodiment, for the adjustment of phase of each wave constituting light, the spatial light modulator 20 is applied. But, other devices of adjusting phase of wave per each pixel such as a digital micro-mirror device (DMD) can be used.

Meanwhile, light reflected by the spatial light modulator 20 penetrates the first beam splitter 51 and then propagates toward the second beam splitter 52 via a lens 63. The second beam splitter 52 allows incident light to penetrate the splitter and to be reflected by the splitter. Here, the penetrated light propagates toward the third beam splitter 53 and the reflected light is incident on the first photo diode 31 via a lens 64. Here, light incident on the first photo diode 31 is used to measure intensity of light incident on disordered medium so as to normalize the transmittance and the reflectance by the measurement of the transmittance and the reflectance.

The third beam splitter 53 makes light which penetrated the second beam splitter 52 and propagate toward a disordered medium (SM) via a lens 66. Then, some of light incident on the disordered medium (SM) penetrates the disordered medium (SM), and the other of the incident light is reflected by the disordered medium (SM) and propagates toward the third beam splitter 53 via a lens 66.

Light reflected by the disordered medium (SM) toward the second beam splitter is reflected by the third beam splitter 53 and then is incident on the second photo diode 32 via a lens 65. Here, by light incident on the second photo diode 32, intensity of light reflected by the disordered medium (SM) is measured.

Meanwhile, light penetrated the disordered medium (SM) is emitted at the other side of the disordered medium (SM) and propagates toward the fourth beam splitter 54 via an object lens 70 and a lens 67. Light penetrated the disordered medium (SM) is reflected by the fourth beam splitter 54 toward the third photo diode 33 and penetrates the fourth beam splitter toward a camera 40.

Here, light which is reflected by the fourth beam splitter 54 and arrived at the third photo diode 33 via lenses 68, 69 is used to measure intensity of light which penetrated the disordered medium (SM). The camera 40 is used to visually discern whether actual transmission characteristics are enhanced in a method of enhancing transmission characteristics of wave by imaging light.

Figure 2:
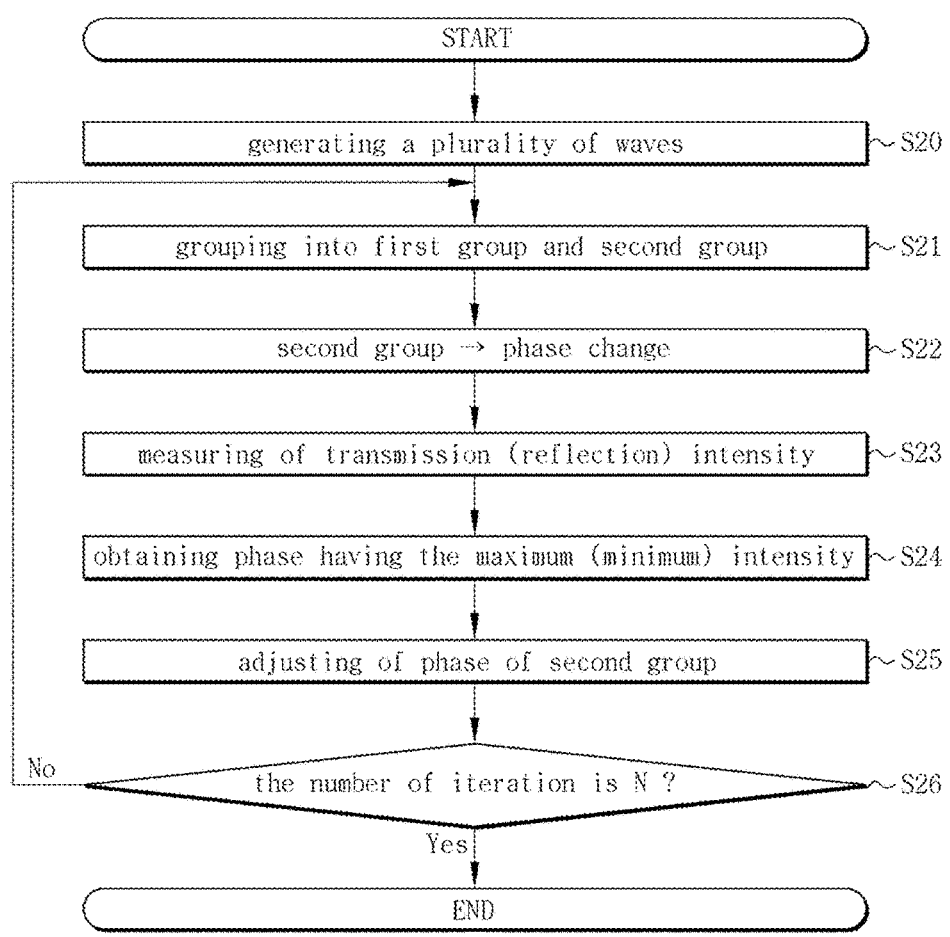
FIG. 2 explains a method of enhancing transmission characteristics of wave according to the invention.

Hereinafter, a method of enhancing transmission characteristics of wave according to the invention will be explained in detail referring to FIG. 2, using the above-explained measuring device.

First, a plurality of waves each of which has random phase is generated (S20). Here, as shown in FIG. 1, when light from the light source 10 is reflected by the spatial light modulator 20, a plurality of waves having random phase are generated. That is, when each pixel constituting the spatial light modulator 20 delays phase of wave, each pixel varies phase randomly.

Here, the spatial light modulator 20 divides a plurality of waves into a first group and a second group (S21). Phase of waves constituting the second group is varied while phase of waves constituting the first group is fixed (S22). Waves which are divided into the first group and the second group are randomly divided into groups.

Figure 3:
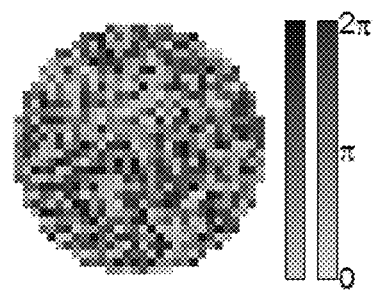
FIG. 3 shows schematically waves constituting the first group and the second group according to the invention.

FIG. 3 shows schematically waves constituting the first group and the second group according to the invention. Blue pixels are the first group and red pixels are the second group. Lightness of the blue and red colors represents phase of each wave. FIG. 3 shows an initial phase of wave and phase of each wave is set randomly and the grouping of the first and second groups is also performed randomly.

As shown above, a plurality of waves divided into the first and second groups by the spatial light modulator 20 are incident on the disordered medium (SM) while phase of waves constituting the second group varies. Then, as described above, some of waves are reflected by the disordered medium (SM) and the others are incident on the disordered medium (SM) and penetrate the disordered medium (SM).

Here, waves reflected by the disordered medium (SM) are incident on the second photo diode 32 in FIG. 1 and waves which penetrated the disordered medium (SM) are incident on the third photo diode 33, thereby intensity of waves are measured. In this regard, waves which penetrated the disordered medium (SM) or are reflected by the disordered medium (SM) are overlapped each other and thus intensity are measured based on the overlapped waves (S23).

Here, intensity of reflected waves or penetrated waves which are measured at the second photo diode 32 or the third photo diode 33 is measured based on the phase variation of waves constituting the second group. That is, intensity of waves is measured according to the phase varied by the spatial light modulator 20.

Regarding intensity of waves measured by the second photo diode 32 or the third photo diode 33, phase having the maximum intensity or minimum intensity according to the phase variation is obtained (S24). Here, in a method for enhancing transmission characteristics of waves according to the invention, in case of measuring intensity of waves reflected by the disordered medium (SM), phase having the minimum intensity according to the phase variation is obtained. Meanwhile, in a method for enhancing transmission characteristics of waves according to the invention, in case of measuring intensity of waves which penetrated the disordered medium (SM), phase having the maximum intensity according to the phase variation is obtained.

FIG. 1 describes measurement of the transmission and the reflection to explain a method of enhancing transmittance of waves according to the invention, but it is noted that any of the transmission and the reflection can be measured.

Here, since intensity measured according to the phase variation of waves constituting the second group exhibits a sinusoidal function, it is not required to measure the maximum value or the minimum value by varying phase in the whole range between 0 to $2\pi$ by means of the spatial light modulator 20. For example, measurements can be made four times at the interval of $\pi/2$ and then phase having the maximum intensity or phase having the minimum intensity can be calculated by fitting.

Then, based on phase having the maximum intensity according to the phase variations (in case of the reflection, phase having the minimum intensity), phase of waves constituting the second group is adjusted (S25). In more detail, as can be explained in the step S20, phase of waves constituting the second group is also set randomly and if phase having the maximum intensity according to the phase variation is determined to be $3\pi/4$, phase of waves constituting the second group is adjusted by $3\pi/4$.

By the above process, phase of waves constituting the second group is adjusted to enhance the transmittance of the disordered medium (SM). For example, in a method of enhancing the transmittance of waves penetrating the disordered medium (SM) according to the invention, when intensity of waves reflected by the disordered medium (SM) is measured, phase of waves constituting the second group is adjusted to be phase of the reflected waves having the minimum intensity so that the reflected waves are minimized and thus the amount of waves incident on the disordered medium (SM) can be increased.

Further, in a method of enhancing the transmittance of waves penetrating the disordered medium (SM) according to the invention, when intensity of waves which penetrates the disordered medium (SM) is measured, phase of waves constituting the second group is adjusted to be phase of the actual penetrating waves having the maximum intensity so that intensity of the actual penetrating waves can be increased.

Meanwhile, by the above process, if phase of waves constituting the second group is adjusted, the steps S21 to S25 are iterated by waves constituting the first group and waves constituting the second group having adjusted phase.

More specifically, if phase of waves constituting the second group is adjusted, waves constituting the first group and waves constituting the second group having adjusted phase are randomly grouped again into the first group and the second group (S21), and then intensity of waves which penetrated the disordered medium (SM) or intensity of waves reflected by the disordered medium (SM) is measured (S23) while phase of waves constituting the re-grouped second group is varied (S22).

Then, phase having the maximum intensity (or the minimum intensity) is obtained (S24) and then phase of waves constituting the re-grouped second group is adjusted based on the obtained phase (S25), thereby enhancing the transmittance of waves.

Figure 4:
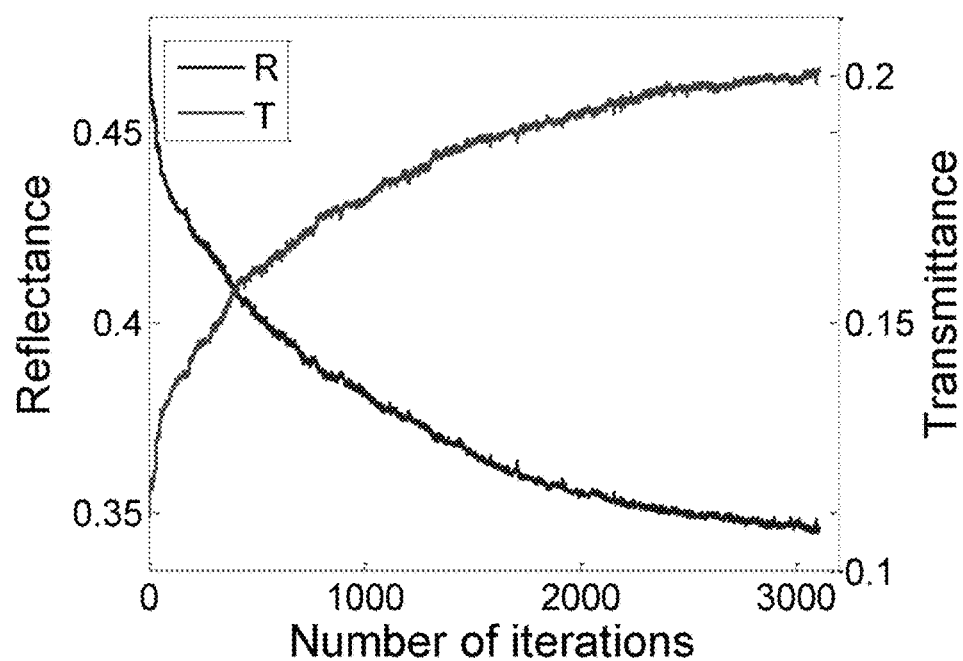
FIG. 4 shows graphs indicating measurement of intensity of waves reflected by the disordered medium (SM) and intensity of waves which penetrated the disordered medium (SM) by a method of enhancing transmission characteristics of wave according to the invention.

FIG. 4 shows graphs indicating measurement of intensity of waves reflected by the disordered medium (SM) and intensity of waves which penetrated the disordered medium (SM). As shown in FIG. 4, by the increase of iterations of the above process, it is noted that intensity of waves penetrating the disordered medium (SM) is increased. On the contrary, as the number of iteration of the above process is increased, it is noted that intensity of waves reflected by the disordered medium (SM) is decreased. Further, it can be noted that with regard to the relation of the reflection and transmission graphs, the pattern of the reflectance decrease is opposite to the pattern of the transmission increase and thus, phase which increases the transmittance can be obtained by measuring intensity of waves reflected by the disordered medium (SM).

FIG. 5($a$) is an image taken by a camera 40 of the measuring device of FIG. 1 before the method of enhancing transmittance of waves according to the invention is applied. FIG. 5($b$) is an image taken by a camera 40 after the method of enhancing transmittance of waves according to the invention is iterated many times, e.g., 3000 times. As shown in FIG. 5, it can be seen visually that an image becomes brighter by the actual penetrating light.

Figure 6:
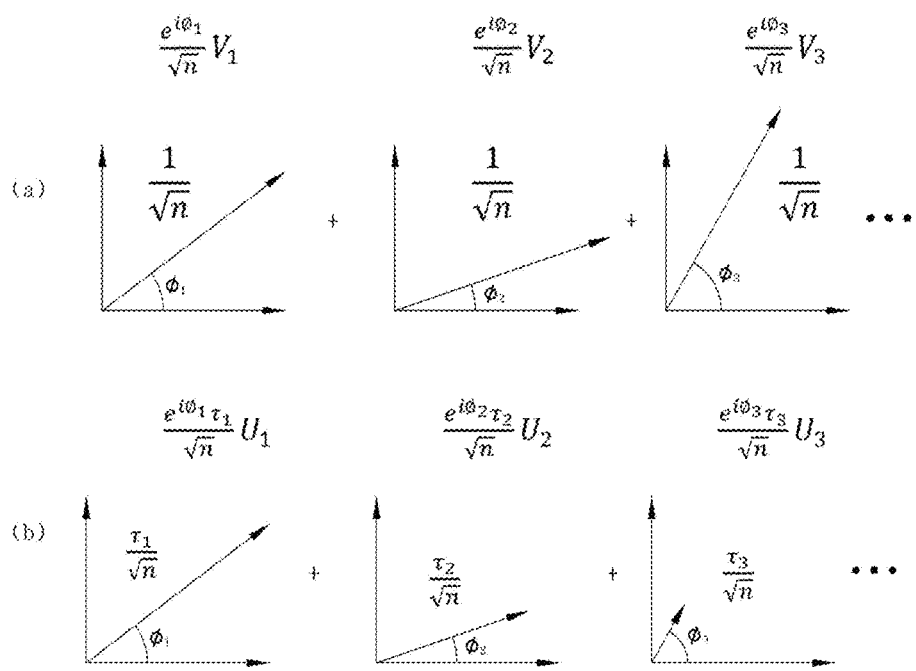
FIGS. 6 and 7 represent the principle that the transmittance is enhanced by the method of enhancing transmittance of waves according to the invention.

Hereinafter, referring to FIG. 6, it will be described how the transmittance is enhanced by the method of enhancing transmittance of waves according to the invention.

If wave of light having random phase is generated by the spatial wave modulator, waves become independent, i.e., orthogonal to each other and the linear summation of orthogonal waves is incident on the disordered medium (SM). The reflection and transmission by the disordered medium (SM) is linear and a plurality of waves which are linear can be represented as a linear summation, i.e., a superposition.

Here, when two waves having the same period are superposed at one point, constructive interference or destructive interference can be generated by the phase difference of the two waves and intensity of wave is increased by constructive interference.

Generally, an arbitrary wave penetrating the disordered medium (SM) make transmittance decreased due to multiple scattering. But, according to random matrix theory, there exist eigenmodes whose transmittance varies according to each disordered medium (SM). Therefore, in some of eigenmodes, there is a very-high transmittance compared to an average transmittance and the transmittance is nearly 1 in theory.

$$tV = U\tau \quad \text{[formula 1]}$$

$$tV_i = \tau_i U_i \quad \text{[formula 2]}$$

$$a = \sum_{i=1}^{n} \frac{e^{i\phi_i}}{\sqrt{n}} V_i \quad \text{[formula 3]}$$

$$ta = \sum_{i=1}^{n} \frac{e^{i\phi_i}\tau_i}{\sqrt{n}} U_i \quad \tau_1 > \tau_2 > \tau_3 > \ldots \quad \text{[formula 4]}$$

Referring to the formulas 1 to 4, random matrix theory will be explained in more detail. In the above formula, t is a transmission matrix, τ is a diagonal matrix, and V and U are a random unitary matrix and represent an incident wave and a transmission wave of the disordered medium (SM), respectively.

$V_i$ and $U_i$ are ith column of V and U, respectively and $\tau_i$ is ith diagonal element of the diagonal matrix. Further, a is an arbitrary incident wave and φ is a phase given randomly.

Here, since V and U are a unit matrix, columns in the matrix are orthogonal each other and are standardized as 1. τ is a positive real number. In formula 2, if a column of V is an incident pattern of light, a corresponding column of U is a transmission pattern and a corresponding element of τ is a size of the penetrated pattern (in case of intensity, $\tau^2$).

In formula 3, α represents an arbitrary incident light and can be represented by formula 3 if the pattern of a plurality of waves having random phase is generated by the spatial light modulator 20 in the invention.

Since all columns of V are orthogonal each other and standardized, each basis of light which can be incident can be represented by a phasor. This actually corresponds to an eigenmode. Therefore, if an arbitrary incident light penetrated, $V_i$ which is a column of V is changed to $U_i$ which is a column of U multiplied by each weighting factor $\tau_i$.

In FIG. 6(a), basis of light incident on the disordered medium (SM) is represented by a phasor and incident light expressed by formula 3 is schematized by a phasor. As shown in FIG. 6(a), phasors of incident light have a different phase, but have a similar size and have the same size $\frac{1}{\sqrt{n}}$ statistically. If light shown in FIG. 6(a) penetrates the disordered medium (SM), light represented by formula 4 is generated as shown in FIG. 6(b). As can be seen in FIG. 6(b), the leftmost phasor is the biggest after the penetration of the disordered medium (SM).

Figure 7:
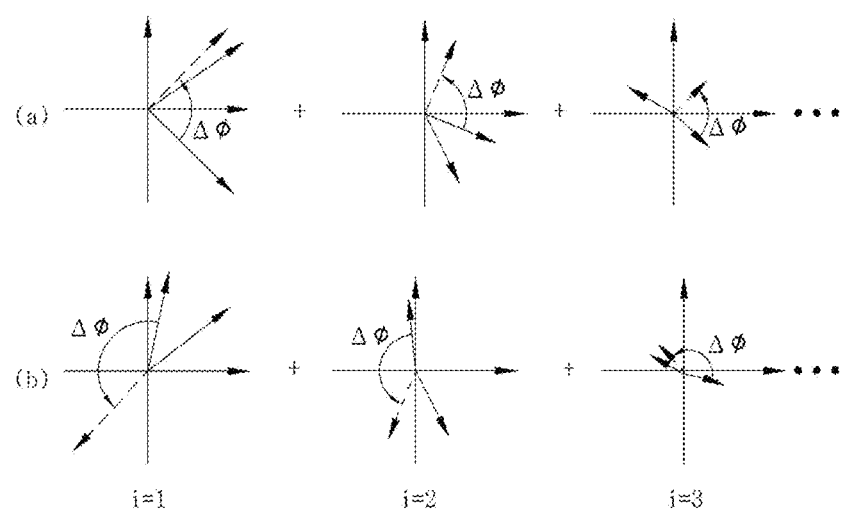

Therefore, as shown in FIG. 7(a), the total intensity of waves measured by sensor such as photo diode is maximized by constructive interference. That is, when phasor (i=1) having the maximum transmittance experiences constructive interference with the same phase, the total intensity increases. Also, for eigenmodes (i=1), the intensity increases substantially by the constructive interference. But, the summation of the other eigenmodes experiences arbitrary interference and thus, the increase of intensity is relatively low.

Therefore, in the method of enhancing transmittance of waves according to the invention, if phase having the maximum of transmission intensity is found iteratively by varying phase of the other group of waves while phase of a certain group of waves, i.e., the first group is fixed, elements of eigenmode having the maximum transmittance are increased, thereby enhancing the transmittance.

FIG. 7(b) shows an example of the reflection. The total intensity of waves measured by the reflection at a sensor such as photo diode is minimized by destructive interference. When phasor (i=1) having the maximum transmittance experiences destructive interference with the opposite phase, the total intensity becomes the minimum.

By the above method, since only the intensity of waves reflected by a disordered medium (SM) or transmitted waves is measured, problems of prior methods of measuring amplitude and phase such as the difficulty of measurement and the need to use additional devices of measuring amplitude and phase simultaneously (e.g., optical element to form a reference light) are solved and it is possible to enhance transmittance of wave which penetrates a disordered medium (SM).

Further, it is possible to selectively use any of waves reflected from the disordered medium (SM) and waves penetrating the disordered medium (SM), and thus transmittance of waves penetrating the disordered medium (SM) can be enhanced and also, transmittance can be enhanced compared to the previous single-point optimization method.

Hereinafter, referring to FIG. 8, a device 100 to which a method of enhancing transmittance of waves according to the invention is applied will be explained. The device 100 according to the invention performs predetermined function by making waves incident on disordered medium (SM). For example, the device 100 according to the invention is configured such that laser is illuminated to a certain cell under human skin.

Figure 8:
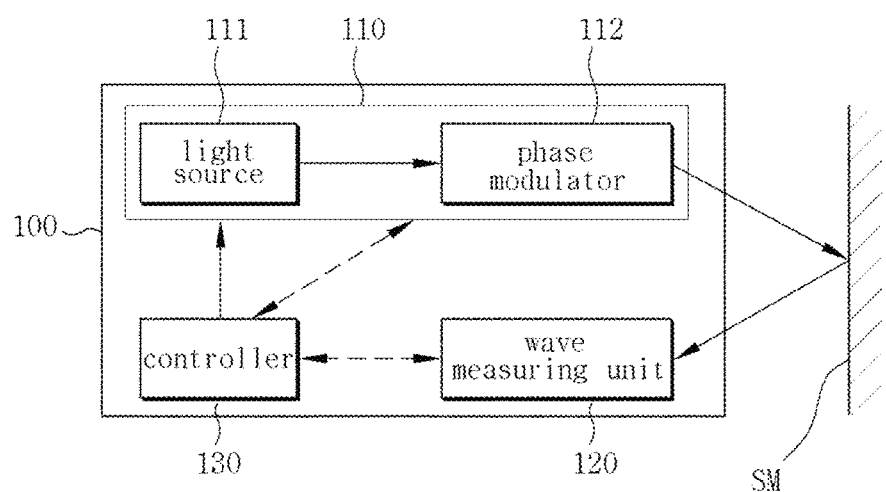
FIG. 8 shows a device of performing predetermined function by introducing wave onto a disordered medium according to the invention.

As shown in FIG. 8, the device according to the invention comprises a wave generating unit 110, a wave measuring unit 120 and a controller 130.

The wave generating unit 110 generates a plurality of waves having random phase and comprises a light source 111 which illuminates light and a phase modulator 112, as shown in FIG. 8. The phase modulator 112 reflects light from the light source 111 and forms a plurality of waves, with phase of each wave being adjusted. Here, the phase modulator 112 can be a spatial light modulator 20 (SLM) as shown in FIG. 1 or a digital micro-mirror device (DMD).

The wave measuring unit 120 measures intensity of waves reflected by the disordered medium (SM). In the embodiment, the wave measuring unit 120 may be a photo diode.

The controller 130 controls the wave generating unit 110 and the wave measuring unit 120 such that the method of enhancing transmittance of wave according to the invention can be applied. In particular, the wave generating unit 110 is controlled such that a plurality of waves generated by the wave generating unit 110 are randomly grouped into the first group and the second group, and phase of waves constituting the second group is varied while phase of waves constituting the first group is fixed.

The controller 130 controls the wave measuring unit 120 such that the wave measuring unit 120 measures intensity of overlapped waves of the first group and the second group based on the variation of phase of waves constituting the second group and the controller controls the wave generating unit 110 such that phase having the minimum intensity according to the variation of phase among intensity measured by the wave measuring unit 120 is obtained and phase of waves constituting the second group are adjusted based on the obtained phase.

If phase of waves constituting the second group by the above process is adjusted, the controller 130 randomly regroups waves constituting the first group and the waves constituting the second group having the adjusted phase and then iterates the above process.

By the above iterations, transmittance of penetrating the disordered medium (SM) is enhanced. In an example of illuminating laser to human skin by the device according to the invention, when laser is illuminated to human skin in the initial process of the device, light having high transmittance to human skin can be illuminated as the process goes on and thus, minimizing the effect of laser on human skin.

In the embodiments, light, i.e., light wave is used as waves applied to the method of enhancing transmittance of waves. Alternatively, other waves such as electromagnetic wave, material wave, sound wave, etc. can be applied to the invention.

It is intended that the foregoing descriptions have described only a few of the many possible implementations of the present invention and that variations or specific embodiments apparent to those skilled in the art within the scope and spirit of the invention are embraced within the scope and spirit of the invention.

| List of Reference Numerals | |
|---|---|
| 10: light source unit | 11: reflective mirror |
| 20: spatial light modulator | 31: first photo diode |
| 32: second photo diode | 33: third photo diode |
| 40: camera | 51: first beam splitter |
| 52: second beam splitter | 53: third beam splitter |
| 54: fourth beam splitter | 100: device |
| 110: wave generator | 120: wave measuring unit |
| 130: controller | |

INDUSTRIAL APPLICABILITY

The method of enhancing transmission characteristics of wave and the device of performing predetermined function by introducing wave onto disordered medium can be applied to devices of performing certain function by introducing wave onto a disordered medium such as a skin treatment equipment using a laser light and an inspection device of inspecting the inside of metal or buildings by means of waves.

The invention claimed is:

1. A method of enhancing transmittance of waves, comprising:
 (a) generating a plurality of waves each of which has random phase;
 (b) grouping randomly the plurality of waves into a first group and a second group;
 (c) introducing the waves onto a disordered medium by fixing phase of waves constituting the first group and varying phase of waves constituting the second group;
 (d) measuring intensity of the waves based on overlapped waves of the first group and the second group which penetrated the disordered medium according to the phase variation of waves constituting the second group;
 (e) obtaining phase having maximum intensity according to the phase variation among intensities measured at the step (d);
 (f) adjusting phase of the waves constituting the second group based on phase obtained at the step (e);
 (g) regrouping randomly waves constituting the first group and waves constituting the second group whose phase was adjusted at the step (f) into the first group and the second group; and
 (h) adjusting phase of waves constituting the regrouped second group by performing the steps (c) to (f) with regard to the regrouped first group and second group, wherein the steps (g) and (h) are performed at least one time.

2. A method of enhancing transmittance of waves, comprising:
 (a) generating a plurality of waves each of which has random phase;
 (b) grouping randomly the plurality of waves into a first group and a second group;
 (c) introducing the waves onto a disordered medium by fixing phase of waves constituting the first group and varying phase of waves constituting the second group;
 (d) measuring intensity of the waves based on overlapped waves of the first group and the second group which are reflected by the disordered medium according to the phase variation of waves constituting the second group;
 (e) obtaining phase having the minimum intensity according to the phase variation among intensities measured at the step (d);
 (f) adjusting phase of the waves constituting the second group based on phase obtained at the step (e);
 (g) regrouping randomly waves constituting the first group and waves constituting the second group whose phase was adjusted at the step (f) into the first group and the second group; and
 (h) adjusting phase of waves constituting the regrouped second group by performing the steps (c) to (f) with regard to the regrouped first group and second group, wherein the steps (g) and (h) are performed at least one time.

3. The method according to claim 1, wherein the waves comprise a light wave, and the steps (a) to (c) are performed by a spatial light modulator (SLM) or a digital micro-mirror device.

4. The method according to claim 1, wherein the waves comprise any one or any combination of any two or more of an electromagnetic wave, a material wave, and a sound wave.

5. The method according to claim 1, wherein during the step (f), phase of waves constituting the second group is adjusted by an amount of phase obtained at the step (e).

6. A device for performing a predetermined function by introducing waves onto a disordered medium, comprising:
 a wave generating unit configured to generate a plurality of waves having random phase;
 a wave measuring unit configured to measure intensity of waves reflected by the disordered medium; and a controller configured to control the wave generating unit based on intensity of waves measured by the wave measuring unit, wherein the controller is further configured to
- (A) group randomly the plurality of waves generated by the wave generating unit into a first group and a second group,
- (B) control the wave generating unit such that phase of waves constituting the first group is fixed and phase of waves constituting the second group is varied,
- (C) control the wave measuring unit such that the wave measuring unit measures intensity of the waves based on overlapped waves of the first group and the second group according to phase variation of waves constituting the second group,
- (D) control the wave generating unit such that phase having minimum intensity according to the phase variation among intensities measured by the wave measuring unit is obtained and phase of the waves constituting the second group is adjusted based on the obtained phase,
- (E) regroup randomly waves constituting the first group and waves constituting the second group whose phase was adjusted into the first group and the second group, and
- (F) control the wave generating unit such that phase of waves constituting the regrouped second group is adjusted by performing the steps (B) to (D) with regard to the regrouped first group and second group, and wherein the steps (E) and (F) are performed at least one time.

7. The device according to claim 6, wherein the wave generating unit comprises a light source, and a phase modulator configured to reflect light from the light source, generate a plurality of waves, and adjust phase of each light wave.

8. The device according to claim 7, wherein the phase modulator comprises a spatial light modulator (SLM) or a digital micro-mirror device.

9. The device according to claim 6, wherein the device is configured to perform the predetermined function by any one or any combination of any two or more of an electromagnetic wave, a material wave, and a sound wave.

10. The device according to claim 6, wherein the controller is further configured to control the wave generating unit such that phase of waves constituting the second group is adjusted by an amount of phase obtained at the step (D).

* * * * *